United States Patent [19]

Hotta et al.

[11] Patent Number: 5,977,396
[45] Date of Patent: Nov. 2, 1999

[54] METHOD FOR RECOVERING ACRYLONITRILE CONTAINED IN A GAS

[75] Inventors: Osamu Hotta; Hiroaki Nakata, both of Kurashiki, Japan

[73] Assignee: Mitsubishi Chemical Corporation, Tokyo, Japan

[21] Appl. No.: 09/185,573

[22] Filed: Nov. 4, 1998

[30] Foreign Application Priority Data

Nov. 6, 1997 [JP] Japan ................................. 9-303870

[51] Int. Cl.⁶ .................................................. C07C 253/00
[52] U.S. Cl. ................................................................ 558/320
[58] Field of Search ................................................ 558/320

*Primary Examiner*—Robert W. Ramsuer
*Assistant Examiner*—Joseph Murray
*Attorney, Agent, or Firm*—Oblon, Spivak, McClelland, Maier & Neustadt, P.C.

[57] ABSTRACT

A method for recovering acrylonitrile contained in a gas, which comprises contacting a gas containing acrylonitrile with water to let the acrylonitrile be absorbed in water, wherein the acrylonitrile is absorbed in water in the presence of a substance having a relative volatility to water at 70° C. of smaller than 1.

15 Claims, 3 Drawing Sheets

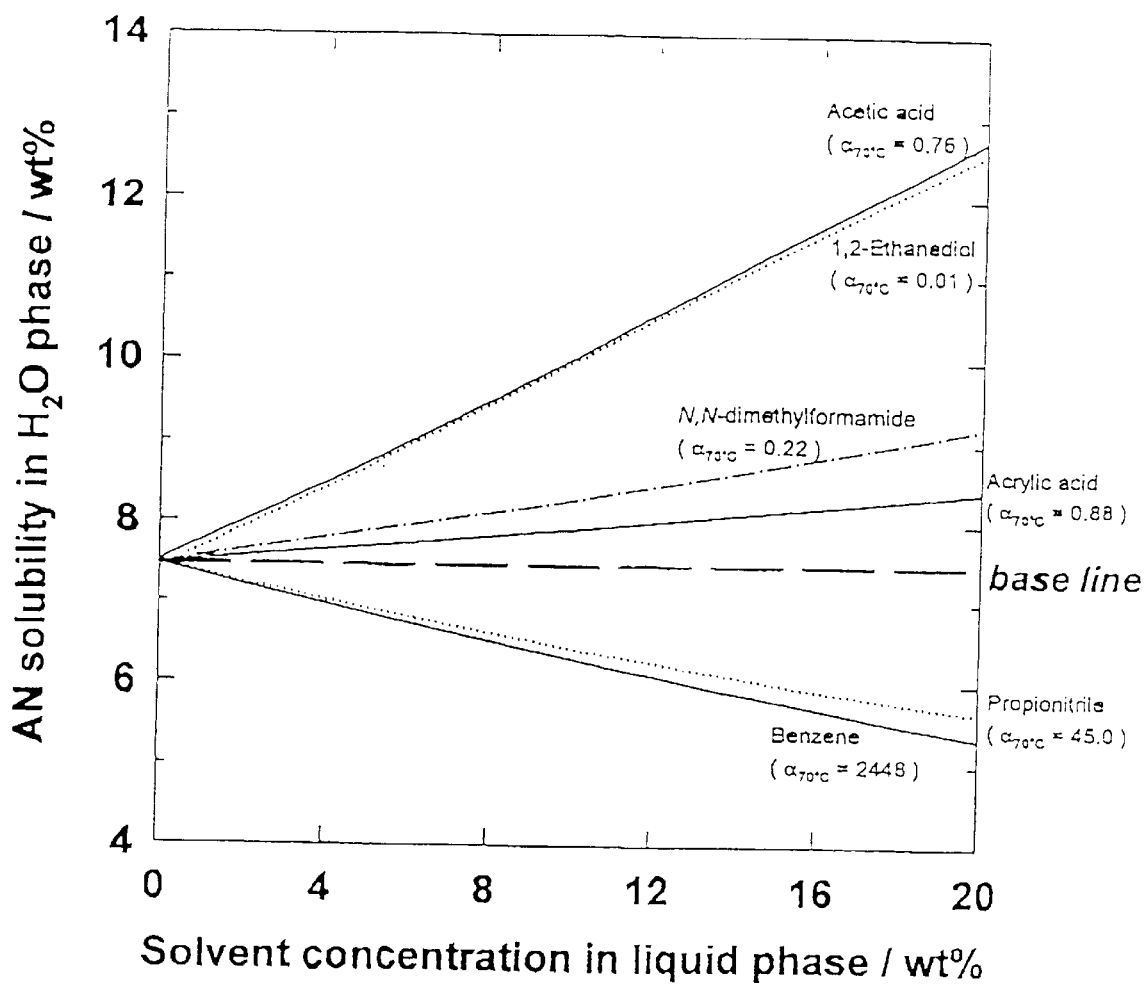
F I G . 3

METHOD FOR RECOVERING ACRYLONITRILE CONTAINED IN A GAS

BACKGROUND OF THE INVENTION

1. Field of the Invention

The present invention relates to an improvement of a method for recovering acrylonitrile by absorbing acrylonitrile contained in a gas in water. Particularly, the present invention relates to a method for accelerating dissolution of acrylonitrile into water, so that when the same amount of an absorbing solvent is employed, the amount of acrylonitrile remaining in the gas can be reduced as compared with a conventional method.

2. Discussion of Background

Acrylonitrile is produced in a large scale by ammoxidation of propylene. Further, a method has recently been developed wherein ammoxidation is carried out using a relatively inexpensive propane as a starting material instead of propylene. In a conventional typical method, propylene, ammonia and air are supplied into a fluidized bed reactor and reacted at a high temperature to form acrylonitrile. An effluent gas containing acrylonitrile from the reactor is firstly washed with an aqueous sulfuric acid solution to remove unreacted ammonia in the form of an aqueous ammonium sulfate solution. Then, the gas is cooled and countercurrently contacted with much amount of water, so that acrylonitrile as well as hydrogen cyanide and other by-product organic substances, will be dissolved in water and separated from the light gas. From the aqueous solution having acrylonitrile, etc., dissolved, purified acrylonitrile is obtained by a proper combination of such means as stripping and distillation. It is important for this method to simultaneously satisfy such requirements that the amount of acrylonitrile remaining in the light gas should be minimized when acrylonitrile contained in the gas is dissolved in water and separated from the light gas and that the concentration of acrylonitrile in the resulting aqueous solution should be as high as possible. Acrylonitrile remaining in the light gas will be wasted as a loss, and the amount being large means a decrease in the yield. Recovery of purified acrylonitrile from the obtained aqueous solution is carried out by a combination of such means as stripping and distillation, as mentioned above. Accordingly, if the acrylonitrile concentration in the aqueous solution is low, the apparatus for stripping and distillation are obliged to be large, and the energy consumption will accordingly be increased.

SUMMARY OF THE INVENTION

Accordingly, it is an object of the present invention to provide a method which simultaneously satisfies the requirements for reducing the amount of acrylonitrile remaining in the light gas and obtaining an aqueous solution containing acrylonitrile in a high concentration, by accelerating dissolution of acrylonitrile in water when acrylonitrile is absorbed by contacting a gas containing acrylonitrile with water.

The present invention provides a method for recovering acrylonitrile contained in a gas, which comprises contacting a gas containing acrylonitrile with water to let the acrylonitrile be absorbed in water, wherein the acrylonitrile is absorbed in water in the presence of a substance having a relative volatility to water at 70° C. of smaller than 1, whereby it is possible to simultaneously satisfy the requirements for reducing the amount of acrylonitrile remaining in the light gas and obtaining an aqueous solution containing acrylonitrile in a high concentration.

BRIEF DESCRIPTION OF THE DRAWINGS

FIG. 3 is a graph showing changes in the solubilities of acrylonitrile in water, when acrylic acid ($\alpha_{70°\ C.}=0.88$), acetic acid ($\alpha_{70°\ C.}=0.76$), 1,2-ethanediol ($\alpha_{70°\ C.}=0.01$), N,N-dimethylformamide ($\alpha_{70°\ C.}=0.22$), propionitrile ($\alpha_{70°\ C.}=45.0$) and benzene ($\alpha_{70°\ C.}=2448$) were, respectively, added to mixtures comprising 50 g of water and 50 g of acrylonitrile, at 25° C.

DETAILED DESCRIPTION OF THE PREFERRED EMBODIMENTS

Figure 1:
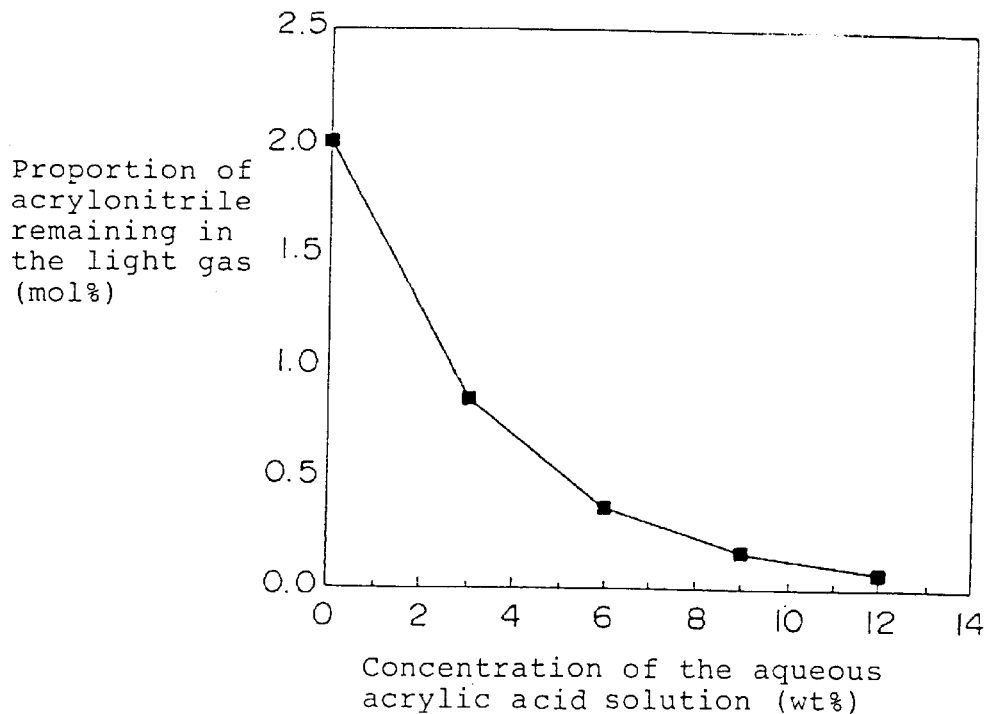
FIG. 1 is a graph showing a relation between the acrylic acid concentration in an aqueous solution and the proportion of acrylonitrile remaining in a light gas to acrylonitrile in a feed gas, when a gas containing about 6.7 mol % of acrylonitrile was contacted with an aqueous acrylic acid solution in an amount of 15 times by weight relative to the acrylonitrile in the feed gas to let the acrylonitrile be absorbed in the aqueous solution using a conventional absorber.

The present invention can be applied to recovery of acrylonitrile from an optional gas containing acrylonitrile. One of preferred applications is recovery of acrylonitrile from a gas obtained by ammoxidation of a $C_{2-8}$ hydrocarbon, preferably a $C_{3-8}$ alkane and/or a $C_{2-8}$ alkene, particularly propane and/or isobutane, or ethylene, propylene and/or isobutylene.

An effluent gas discharged from an ammoxidation reactor contains in addition to acrylonitrile as the main product, by-product organic substances such as hydrogen cyanide, carbon dioxide formed by a combustion reaction as well as unreacted hydrocarbons, ammonia and oxygen. Further, when air is employed as the oxygen source, nitrogen derived from the air will be contained in a large amount. Usually, after removing unreacted ammonia from this gas by washing with an aqueous sulfuric acid solution or by other method, the gas is subjected to recovery of acrylonitrile by the present invention.

In the present invention, a gas containing acrylonitrile is contacted with water in the presence of a substance having a relative volatility to water at 70° C. of smaller than 1, to let the acrylonitrile contained in the gas dissolve in the water.

In the present invention, the relative volatility to water is meant for a relative volatility ($\alpha$) to water in infinite dilution.

The substance having a relative volatility to water at 70° C. ($\alpha_{70°\ C.}$) of smaller than 1 may, for example, be acrylic acid, acetic acid, 1,2-ethanediol, 1,2-butanediol, 2,3-butanediol, N,N-dimethylformamide, N,N-dimethylacetamide, dimethylsulfoxide, 1,2-propanediol, 1,3-propanediol, N-methyl-2-pyrrolidone or N-methylacetamide. In Table 1, the relative volatility to water at 70° C. of each of these substances is shown. For further reference, as examples for a substance having a relative volatility ($\alpha_{70°\ C.}$) of larger than 1, the $\alpha_{70°\ C.}$ values of propionitrile and benzene are also shown in Table 1.

TABLE 1

| Names of substances | $\alpha_{70°\ C.}$ |
| --- | --- |
| Acrylic acid | 0.88 |
| Acetic acid | 0.76 |
| 1,2-Ethanediol | 0.01 |
| 1,2-Buthanediol | 0.02 |
| 2,3-Buthanediol | 0.06 |
| N,N-Dimethylformamide | 0.22 |
| Dimethylsulfoxide | 0.01 |
| 1,2-Propanediol | 0.04 |
| 1,3-Propanediol | 0.02 |
| N-Methyl-2-pyrrolidone | 0.05 |
| N-Methylacetamide | 0.02 |
| Propionitrile | 45.0 |
| Benzene | 2448 |

Among them, particularly preferred are acrylic acid and acetic acid.

In the present invention, the amount of the substance with $\alpha_{70°\ C.}<1$ is not particularly limited. However, it is usually preferably at least 0.1 wt % based on the water. Further, it is usually preferably at most 12 wt % based on the water.

For example, in the case of acrylic acid, it is usually present in an amount of at least 1 wt %, preferably from 2 to 12 wt %, more preferably from 3 to 10 wt %, most preferably from 4 to 8 wt %, based on the water.

In the case of acetic acid or other substance, it is usually present in an amount of at least 0.1 wt %, preferably from 0.2 to 5 wt %, more preferably from 0.3 to 4 wt %, based on the water.

By the presence of the substance with $\alpha_{70°\ C.}<1$ during the contact of the gas containing acrylonitrile with water, the solubility of acrylonitrile in water increases. Further, the larger the concentration of the substance with $\alpha_{70°\ C.}<1$ in the water is, the higher the solubility of acrylonitrile in the water becomes.

Further, the substance with $\alpha_{70°\ C.}<1$ will accompany the water (the column bottom side) when the acrylonitrile and the water are separated in the next acrylonitrile recovery column, whereby it can easily be separated from the acrylonitrile, and purification of acrylonitrile in the subsequent purification step can be carried out efficiently.

On the other hand, in a case where a substance having a volatility of not being $\alpha_{70°\ C.}<1$, is present, such a substance will accompany the acrylonitrile (the column top side) when the acrylonitrile and the water are separated in the next acrylonitrile recovery column, whereby further precise separation from the acrylonitrile will be required, and it tends to be difficult to carry out the purification of acrylonitrile in the subsequent purification step efficiently.

Further, for example, in a case where water to absorb acrylonitrile at an absorber is recycled for use, the substance having a volatility of not being $\alpha_{70°\ C.}<1$ will be discharged out of the acrylonitrile recovery section as accompanying the acrylonitrile at a following recovery column, and in order to maintain its concentration within a required range, it will be necessary to supplement such a substance occasionally, and largely, such being economically problematic. Whereas the substance with $\alpha_{70°\ C.}<1$, will be recycled mostly as accompanying the absorbent water, whereby it is not required to supplement it largely.

FIG. 1 shows a sample of a relation between the concentration of acrylic acid in water and the proportion of acrylonitrile remaining in a light gas emitted from the top of an absorber, when a gas containing acrylonitrile supplied from a lower portion of an absorber and an aqueous acrylic acid solution of 5° C. supplied from an upper portion, were counter-currently contacted. Here, the proportion (%) of acrylonitrile remaining in a light gas is the ratio of the mols of acrylonitrile in the non-condensed gas emitted from the top of the absorber to the mols of acrylonitrile in the gas supplied to the absorber. The composition of the supplied gas was such that acrylonitrile was about 6.7 mol %, nitrogen about 88.2 mol %, and carbon dioxide about 4.0 mol %, and it was supplied to the absorber under a pressure of a 0.5 kg/cm$^2$G and emitted from the column under a pressure of 0.35 kg/cm$^2$ G. The total amount of acrylic acid and water supplied was 15 times by weight relative to the acrylonitrile in the feed gas.

As is evident from FIG. 1, the amount of acrylonitrile remaining in the light gas emitted from the top of the absorber, decreased as the concentration of acrylic acid increased, and the decreasing amount was especially remarkable in a region where the concentration of acrylic acid was thin.

Of course, the graph in FIG. 1 may change depending upon the operation conditions of the absorber. However, the influence of the concentration of acrylic acid shown by the graph in FIG. 1, particularly the tendency that a large effect is obtainable in a region where the concentration of acrylic acid is relatively thin, will be maintained. For example, when the ratio of aqueous acrylic acid solution to the acrylonitrile, which is influential over the amount of acrylonitrile remaining in the light gas, is decreased from 15 times by weight to 14 times by weight, the graph in FIG. 1 will change to one in FIG. 2. Namely, if absorption is carried out simply by water, more than 8% of acrylonitrile will remain in the light gas, such being not practical. Whereas, when absorption is carried out by an aqueous solution containing 8 wt % of acrylic acid, based on water, acrylonitrile remaining in the light gas will decrease to 2% which is equal to a case where absorption is carried out in water of 15 times by weight. Further, if the temperature of water is lowered, or if the concentration of acrylonitrile in the feed gas is increased relatively by reducing the nitrogen content in the feed gas, the curve in the Figure moves downwardly. In the present invention, acrylonitrile contained in the gas can be absorbed with an aqueous solution containing at least 1 wt % of acrylic acid based on water. Preferably, the acrylic acid is present in an amount of at least 3 wt %, particularly preferably at least 4 wt %, based on water.

Figure 2:
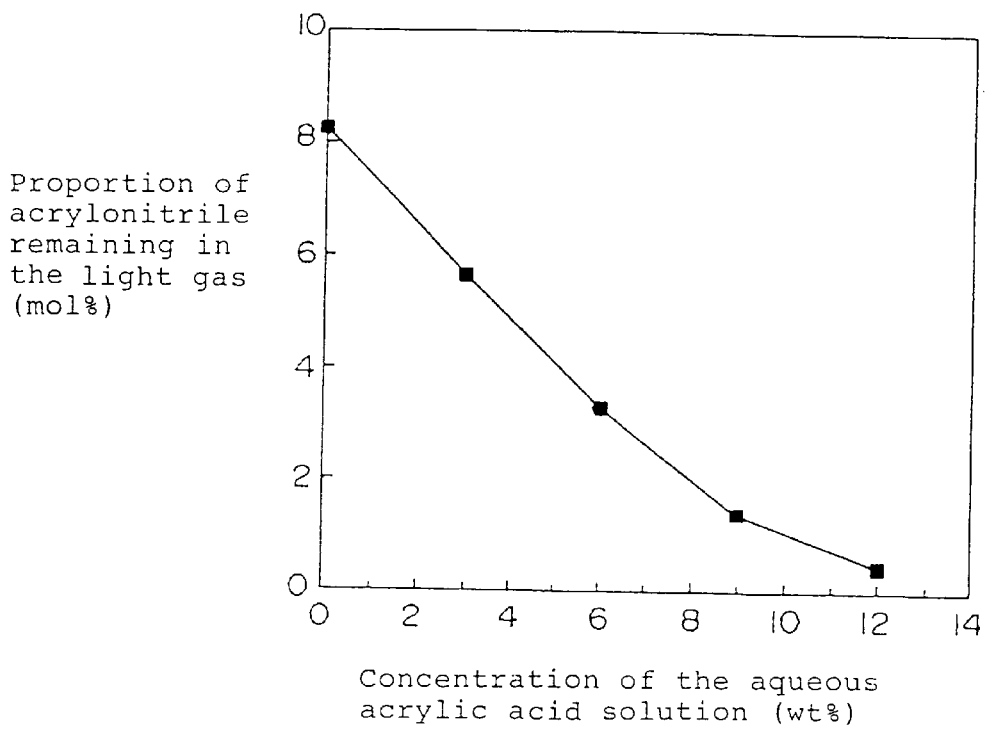
FIG. 2 is a graph similar to FIG. 1 in a case where an aqueous acrylic acid solution in an amount of 14 times by weight relative to the acrylonitrile in the feed gas, was contacted.
Figure 4:
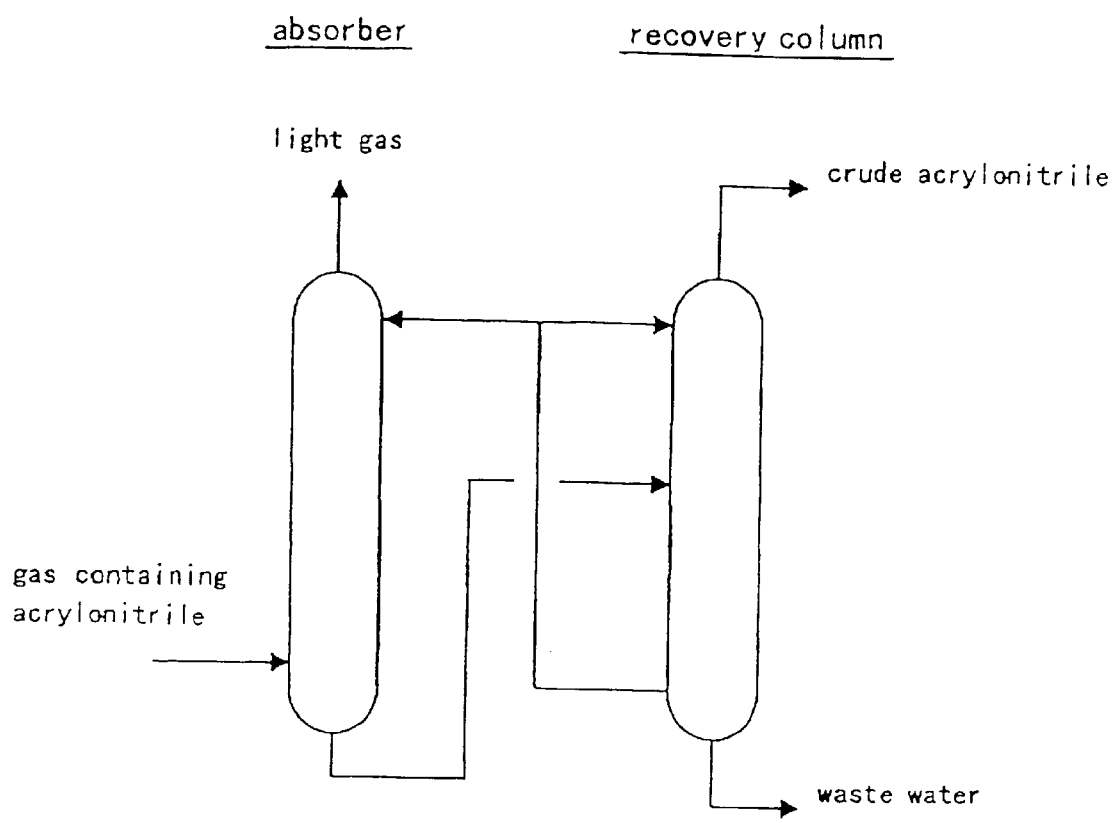
FIG. 4 is a schematic view showing an acrylonitrile absorber and an acrylonitrile recovery column, which can be used in the present invention.

As is evident from FIGS. 1 and 2, the higher the concentration of acrylic acid, the better the absorption of acrylonitrile. On the other hand, there will be a problem that acrylic acid in the aqueous acrylic acid solution tends to undergo stripping by the gas emitted from the absorber, whereby the concentration of acrylic acid in the gas tends to increase, thus leading to a loss of acrylic acid. From this viewpoint, the concentration of acrylic acid is restricted, and it is present usually in an amount of at most 12 wt % based on water. With a view to suppressing the loss of acrylic acid, acrylic acid is present preferably in an amount of at most 10 wt %, more preferably at most 8 wt %, based on water. To satisfy both promotion of absorption of acrylonitrile and suppression of the loss of acrylic acid, acrylic acid may be present most preferably in an amount of from 4 to 8 wt % based on water.

Further, FIG. 3 shows changes in the solubilities of acrylonitrile in water, when acrylic acid ($\alpha_{70°\ C.}=0.88$), acetic acid ($\alpha_{70°\ C.}=0.76$), 1,2-ethanediol ($\alpha_{70°\ C.}=0.01$), N,N-dimethylformamide ($\alpha_{70°\ C.}=0.22$), propionitrile ($\alpha_{70°\ C.}=45.0$) and benzene ($\alpha_{70°\ C.}=2448$) were, respectively, added to mixtures comprising 50 g of water and 50 g of acrylonitrile, at 25° C.

When acrylonitrile in the gas is to be absorbed in water, it is usual that the gas containing acrylonitrile is cooled to at most 100° C., preferably at most 30° C., and then introduced from a lower portion of the absorber. Water and the substance with $\alpha_{70°\ C.}<1$ are cooled usually to at most 10° C., preferably at most 5° C., then introduced from an upper portion of the absorber and counter-currently contacted with the gas containing acrylonitrile, in the absorber, whereby water-soluble components in the gas, such as acrylonitrile, are absorbed in water. The solution having acrylonitrile absorbed, is discharged from the bottom of the absorber via a conduit, and then introduced to the acrylonitrile recovery column. On the other hand, the non-condensable gas is discharged as off-gas from the top of the absorber.

As the absorber, a conventional one such as a tray column or a packed column, may be used. In a conventional case where acrylonitrile is absorbed by water, the obtained aqueous solution from the absorber bottom is subjected to extraction distillation at the acrylonitrile recovery column using water as extracting agent to recover water which does not contain acrylonitrile, etc, from the acrylonitrile recovery column and a part of such water is usually recycled for absorption of acrylonitrile. In this invention, also in a case where the aqueous acrylic acid solution is used as an absorbing liquid, the acrylonitrile etc. and the aqueous acrylic acid solution can be separated in exactly the same manner by extraction distillation using the aqueous acrylic acid solution as an extracting agent. The boiling point of acrylic acid is substantially higher than the acrylonitrile, etc., whereby separation by distillation is easy.

As described in detail in the forgoing, according to the present invention, acrylonitrile can easily be separated from a gas containing acrylonitrile, such as a gas obtained by ammoxidation of a $C_{2-8}$ hydrocarbon.

The present invention is useful, for example, for recovery of acrylonitrile from a reaction solution containing acrylonitrile, obtained by a method wherein propylene, ammonia and oxygen are subjected to ammoxidation in a presence of a solid oxide catalyst, or a method wherein propane, ammonia and oxygen are subjected to ammoxidation in the presence of a solid oxide catalyst. The catalyst to be used for such ammoxidation may preferably be a catalyst containing molybdenum and/or vanadium. Specific examples of such a catalyst include a catalyst obtained by mechanically mixing a V-Sb-W type oxide and Mo-Bo-Ce-W type oxide (JP-A-64-38051), a Mo-Ag-Bi-V type catalyst (JP-A-3-58961), a Mo-V-Sn-Bi-P type catalyst (JP-A-4-247060), a Mo-Cr-Te type catalyst (U.S. Pat. No. 5,171,876), a double oxide catalyst comprising Mo and an element such as Mn or Co (JP-A-5-194347), a Mo-V-Te (Sb)-X type catalyst (JP-A-2-257, JP-A-5-148212, JP-A-3-104382), a Mo-Cr-Bi-X-Y type catalyst (JP-A-6-116225), a V-Sb type catalyst (JP-A-1-268668, JP-A-2-180637), a V-Sb-W-P type catalyst (JP-A-2-95439), and a V-Sb-Sn-Cu type catalyst (JP-A-4-275266), and so on. Particularly preferred is a catalyst containing Mo, V, Te(Sb) and Nb as essential constituting components, or a catalyst containing V and Sb as essential constituting components.

What is claimed is:

1. A method for recovering acrylonitrile contained in a gas, which comprises contacting a gas containing acrylonitrile with water to let the acrylonitrile be absorbed in water, wherein the acrylonitrile is absorbed in water in the presence of a substance having a relative volatility to water at 70° C. of smaller than 1.

2. The method according to claim 1 wherein the substance having a relative volatility to water at 70° C. of smaller than 1 is present in an amount of at least 0.1 wt % based on the water.

3. The method according to claim 2 wherein the substance having a relative volatility to water at 70° C. of smaller than 1 is present in an amount of at most 12 wt % based on the water.

4. The method according to claim 1, wherein the substance having a relative volatility to water at 70° C. of smaller than 1 is at least one substance selected from the group consisting of acrylic acid, acetic acid, 1,2-ethanediol, 1,2-butanediol, 2,3-butanediol, N,N-dimethylformamide, N,N-dimethylacetamide, dimethylsulfoxide, 1,2-propanediol, 1,3-propanediol, N-methyl-2-pyrrolidone and N-methylacetamide.

5. The method according to claim 1, wherein the substance having a relative volatility to water at 70° C. of smaller than 1 is acetic acid.

6. The method according to claim 5, wherein the acetic acid is present in an amount of from 0.2 to 5 wt % based on the water.

7. The method according to claim 1, wherein the substance having a relative volatility to water at 70° C. of smaller than 1 is acrylic acid.

8. The method according to claim 7, wherein the acrylic acid is present in an amount of at least 1 wt % based on the water.

9. The method according to claim 8, wherein the acrylic acid is present in an amount of from 2 to 12 wt % based on the water.

10. The method according to claim 1, wherein the gas containing acrylonitrile is a gas obtained by ammoxidation of a $C_{2-8}$ hydrocarbon.

11. The method according to claim 1, wherein the gas containing acrylonitrile is one having ammonia removed from a gas obtained by ammoxidation of a $C_{2-8}$ hydrocarbon.

12. The method according to claim 1, wherein the gas containing acrylonitrile is a gas obtained by ammoxidation of a $C_{3-8}$ alkane and/or a $C_{2-8}$ alkene.

13. The method according to claim 12, wherein the alkane is propane and/or isobutane.

14. The method according to claim 12, wherein the alkene is ethylene, propylene and/or isobutylene.

15. The method according to claim 1, wherein after the acrylonitrile is absorbed in water, the acrylonitrile and the water are separated in a purification step.

* * * * *